US012515004B2

(12) United States Patent
Spector et al.

(10) Patent No.: US 12,515,004 B2
(45) Date of Patent: Jan. 6, 2026

(54) METHOD AND SYSTEM OF SENSING AIRFLOW AND DELIVERING THERAPEUTIC GAS TO A PATIENT

(71) Applicant: INCOBA, LLC, Wildwood, MO (US)

(72) Inventors: Lawrence C. Spector, Austin, TX (US); Alonzo C. Aylsworth, Wildwood, MO (US); Mark Doane, Millstadtt, IL (US)

(73) Assignee: INCOBA, LLC, Wildwood, MO (US)

( * ) Notice: Subject to any disclaimer, the term of this patent is extended or adjusted under 35 U.S.C. 154(b) by 939 days.

(21) Appl. No.: 17/642,878

(22) PCT Filed: Sep. 22, 2020

(86) PCT No.: PCT/US2020/051932
§ 371 (c)(1),
(2) Date: Mar. 14, 2022

(87) PCT Pub. No.: WO2021/061607
PCT Pub. Date: Apr. 1, 2021

(65) Prior Publication Data

US 2022/0395663 A1 Dec. 15, 2022

Related U.S. Application Data

(60) Provisional application No. 62/904,062, filed on Sep. 23, 2019.

(51) Int. Cl.
*A61M 16/00* (2006.01)
*A61M 16/06* (2006.01)

(52) U.S. Cl.
CPC .... *A61M 16/0677* (2014.02); *A61M 16/0051* (2013.01); *A61M 16/024* (2017.08)

(58) Field of Classification Search
CPC .......... A61M 16/0677; A61M 16/0051; A61M 16/024; A61M 2016/0039;
(Continued)

(56) References Cited

U.S. PATENT DOCUMENTS 3,662,751 A 5/1972 Barkalow et al.
4,747,403 A * 5/1988 Gluck ................ A61M 16/127 128/205.24
5,301,663 A * 4/1994 Small, Jr. .......... A61M 15/0015 128/200.21
6,237,594 B1 * 5/2001 Davenport ........ A61M 16/0677 128/204.26
8,656,913 B2 2/2014 Kroupa
10,953,172 B2 3/2021 Aylsworth et al.
(Continued)

FOREIGN PATENT DOCUMENTS

WO 2008077003 A1 6/2008

OTHER PUBLICATIONS

International Search Report and Written Opinion of PCT/US2020/051932, mailed Dec. 14, 2020.

*Primary Examiner* — Brandy S Lee
*Assistant Examiner* — Tina Zhang
(74) *Attorney, Agent, or Firm* — Dickinson Wright PLLC; Mark E. Scott

(57) ABSTRACT

Sensing airflow and delivering therapeutic gas to a patient. At least one example embodiment is a method including: sensing, by a delivery device, that multiple breathing orifices are open to flow; and during a plurality of subsequent inhalations in which multiple breathing orifices are open to flow; and delivering, by the delivery device, a bolus of therapeutic gas to only one breathing orifice during each inhalation, and alternating delivery location in subsequent inhalations. The example delivering may further comprise: supplying therapeutic gas only from an accumulator during a first portion each inhalation; dispensing therapeutic gas from the accumulator and from a pressure regulator during a second portion of each inhalation, the second portion immediately subsequent to the first portion.

23 Claims, 6 Drawing Sheets

(58) Field of Classification Search

CPC .. A61M 2016/0021; A61M 2016/0027; A61M 2205/18; A61M 2205/3331; A61M 2205/3334; A61M 2205/42; A61M 2206/11; A61M 2210/0618; A61M 2210/0625; A61M 16/202; A61M 2202/0208; A61M 16/01; A61M 16/10; A61M 16/104; A61M 16/18; A61M 2016/0015; A61M 16/107; A61M 16/00; A61B 5/087; A61B 5/097

USPC ............ 128/204.18, 204.21, 203.12, 205.24, 128/204.26, 200.24; 600/529

See application file for complete search history.

(56) References Cited

U.S. PATENT DOCUMENTS

| | | | | |
|---|---|---|---|---|
| 2006/0113690 | A1* | 6/2006 | Huddart ............ | A61M 16/1075 261/129 |
| 2008/0302363 | A1 | 12/2008 | Kroupa | |
| 2010/0051029 | A1* | 3/2010 | Jafari ................ | A61M 16/0051 128/204.23 |
| 2010/0139656 | A1* | 6/2010 | Friberg ............... | A61M 16/205 128/205.24 |
| 2011/0041848 | A1 | 2/2011 | Stone et al. | |
| 2013/0102828 | A1 | 4/2013 | Knudsen et al. | |
| 2017/0203062 | A1 | 7/2017 | Aylsworth et al. | |
| 2017/0340851 | A1* | 11/2017 | Allum ............... | A61M 16/0672 |
| 2018/0078726 | A1* | 3/2018 | Barraclough ..... | A61M 16/0666 |
| 2019/0134340 | A1 | 5/2019 | Nebrigac | |

* cited by examiner

METHOD AND SYSTEM OF SENSING AIRFLOW AND DELIVERING THERAPEUTIC GAS TO A PATIENT

CROSS-REFERENCE TO RELATED APPLICATIONS

This application is a 35 U.S.C. § 371 national phase of PCT International Application No. PCT/US2020/051932, filed Sep. 22, 2020, which claims the benefit of U.S. Provisional Patent Application No. 62/904,062 filed Sep. 23, 2019, titled "Method And System Of Sensing Airflow And Delivering Therapeutic Gas To A Patient," and incorporated by reference herein as if reproduced in full below.

BACKGROUND

Patients with respiratory ailments may be required to breathe therapeutic gas, such as oxygen. The therapeutic gas may be delivered to the patient from a therapeutic gas source by way of a nasal cannula.

Delivery of therapeutic gas to a patient may be continuous, or in a conserve mode. In continuous delivery, the therapeutic gas may be supplied at a constant flow rate throughout the patient's breathing cycle. A significant portion of the therapeutic gas provided in continuous delivery is wasted (i.e., the therapeutic gas delivered during exhalation of the patient is lost to atmosphere). In order to overcome the wastefulness of continuous delivery, related-art devices may operate in conserve mode using a conserver system.

A conserver system may be a device which senses a patient's inspiration, and delivers a bolus of therapeutic gas at relatively higher pressure (e.g., 25 PSIG) and high velocity during each inhalation. By delivering therapeutic gas only during inhalation, the amount of therapeutic gas lost to atmosphere may be reduced.

BRIEF DESCRIPTION OF THE DRAWINGS

For a detailed description of the various embodiments, reference will now be made to the accompanying drawings in which.

DEFINITIONS

Figure 1:
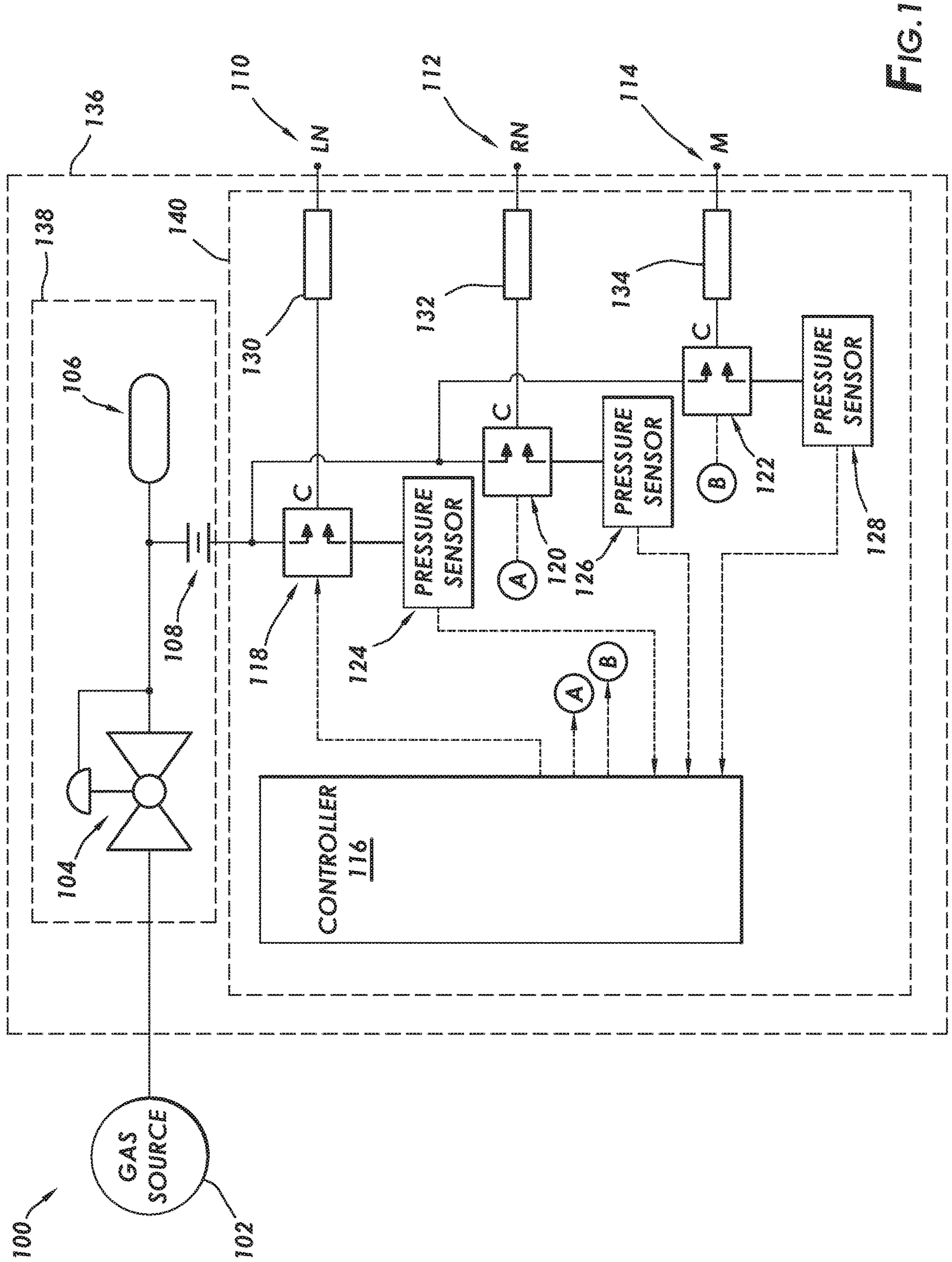
FIG. 1 shows a delivery system in accordance with at least some embodiments.

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . " Also, the term "couple" or "couples" is intended to mean either an indirect or direct electrical or mechanical connection. Thus, if a first device couples to a second device, that connection may be through a direct connection, or through an indirect connection via other devices and connections.

"Nares" shall mean the nostrils of a patient.

"Naris" shall mean a single nostril of a patient, and is the singular of "nares."

"Flow state of breathing orifices" shall refer to a flow state of a set of breathing orifices at a particular point in time. For example, considering only the nares of a patient as the set of breathing orifices, each nare can be open to flow (designated as "O" below) or blocked to flow (designated as "B" below), and thus the flow state of the breathing orifices in the example set being the left nare and the right nare (in that order) may take any one of the following states: {O, O}, {O, B}, {B, O}, and {B, B}. Similarly, in a set being the left nare, the right nare, and mouth (in that order) the flow state may take any one of the following flow states: {O, O, O}, {O, B, O}, {B, O, O}, {B, B, O}, {O, O, B}, {O, B, B}, and {B, O, B}.

"Substantially", in relation to a recited volume, shall mean within +/−10% of the recited volume.

"About," in reference to a recited value, shall mean the recited value plus or minus +/− ten percent (10%).

"Controller" shall mean, alone or in combination, individual circuit components, an application specific integrated circuit (ASIC), a microcontroller with controlling software, a digital signal processor (DSP), a processor with controlling software, a field programmable gate array (FPGA), or a programmable logic device (PLD), configured to read inputs and drive outputs responsive to the inputs.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of the embodiment, and not intended to intimate that the scope of the disclosure, including the claims, is limited to that embodiment.

The various embodiments are directed to delivery of therapeutic gas by way of bolus control. More particularly, various example embodiments control, on a breath-t-breath breath-to-breath basis, the location of bolus delivery based on the flow state of breathing orifices of the patient. More particularly still, when two or more breathing orifices are open to flow, the various example embodiments alternate delivery location flow. At the selected delivery location the example embodiments balance considerations of gas velocity, efficacy of delivery to the lungs, discomfort and/or damage to mucosal tissue, and noise associated with the delivery of the therapeutic gas.

Designers of bolus-type therapeutic gas delivery systems balance a host of factors when designing such systems. For example, from the standpoint of efficacy of therapeutic gas delivered to the lungs, the earlier in an inhalation the therapeutic gas is delivered, and the greater the volume of the gas delivered earlier in the inhalation, the greater the efficacy of the therapeutic gas to the patient. The timing and volume considerations for delivery of therapeutic gas favor higher pressure and/or higher velocity delivery of therapeutic gas to the breathing orifices.

Another consideration in the design of therapeutic gas delivery system is the noise or sound associated with the delivery. Many therapeutic gas delivery systems are designed and constructed for use not only during waking hours of the patient, but also during sleep. The higher the pressure of each bolus, and the higher the velocity of the therapeutic gas of the bolus, the louder the sound or noise associated with the system. Thus, sound and/or noise considerations favor lower pressure and/or lower velocity of bolus delivery of therapeutic gas to the breathing orifices.

Yet another consideration in the design of bolus-type therapeutic gas delivery systems is damage and/or discomfort of the patient caused by the therapeutic gas delivery. That is, while higher pressure and/or higher velocity of therapeutic gas may increase efficacy of the gas delivered to the lungs, the higher pressure and/or higher velocity may cause physical damage (e.g., tearing) of the mucosal membranes within the nose. Moreover, the higher pressure and/or the higher the velocity cause more pronounced drying of the mucosal tissue. Damage and/or dryness of the mucosal tissue may cause physical damage to the mucosal membranes, and damage and/or dryness may also causes swelling of the mucosal tissue. Swelling increases the resistance to airflow, which further exacerbates the therapeutic gas delivery problem.

In designing bolus-type therapeutic gas delivery systems to balance these considerations, the inventors of the current specification identified various shortcomings of related-art devices. In particular, related-art devices assume that pressure regulators can quickly respond to pressure drops caused by bolus delivery. However, currently available pressure regulators have response delay or lag, and such lag results in lowered pressure during bolus delivery. The lowered pressure may result in providing less than the prescribed titration volume of therapeutic gas delivered. The lowered pressure may also result in providing the therapeutic gas at lower velocity. Delivering less than the prescribed titration volume and/or lower velocity means less therapeutic gas is delivered deep into the lungs, and thus results in lower efficacy.

Moreover, related-art devices fail to consider turbulence in therapeutic gas flow caused by tubing connections, bends in tubing connections, and flow through control valves. That is, even if hypothetically assumed related-art devices can consistently deliver the prescribed titration volume at each inhalation (which is not necessarily true), the turbulence of the therapeutic gas flow results in lower average velocity in movement toward the lungs. Similarly, a turbulent flow of therapeutic gas flowing through the nose may result in greater irritation of the mucosal tissue, as compared to a laminar flow through the nose.

Thus, at least some example embodiments are directed to delivery of therapeutic gas to a patient which addresses (at least in part) these considerations. More particularly, example embodiments address shortfalls in delivery of therapeutic gas by delivering a bolus of therapeutic gas to only one breathing orifice (e.g., a single naris) during each inhalation if multiple breathing orifices are open to flow. With respect to each bolus delivered to a breathing orifice, an initial portion of the bolus is supplied from therapeutic gas in an accumulator to account for lag or response time of a pressure regulator. Thereafter, a subsequent portion of the bolus is dispensed from a combination of therapeutic gas through the pressure regulator and the therapeutic gas in the accumulator. In this way, the pressure of the therapeutic gas remains within a predetermined range of pressures during bolus delivery, which better ensures delivery of the prescription titration volume, and better ensures sufficient velocity.

FIG. 1 shows a system 100 in accordance with at least some embodiments. The example system 100 comprises a gas source 102. The gas source 102 may take any suitable form, such as a gas cylinder or a permanent high-pressure supply system, such as in a hospital. In many cases, the gas source 102 supplies therapeutic gas (e.g., oxygen) at a pressure higher than needed or desired for delivery to a patient, and thus the example system 100 comprises a control valve or pressure regulator 104. The example pressure regulator 104 may take any suitable form. In the case of the gas source 102 being a gas cylinder of therapeutic gas, the gas source 102 may provide at relatively high pressure (e.g., 2000 PSIG), thus the pressure regulator 104 reduces the pressure for delivery to the patient. In one example system, the downstream or regulated pressure is 25 PSIG, but higher and lower pressures may be used. Higher pressures increase sound or noise associated with the delivery, and also increase velocity of therapeutic gas delivered. Oppositely, lower pressures decrease sound or noise associated with the delivery, and also decrease velocity of therapeutic gas delivered. The example 25 PSIG provided by the pressure regulator 104, possibly in combination with other features discussed more below, represents a balance between noise generation consideration and velocity of therapeutic gas delivery. Other designs may make different tradeoffs, and thus the 25 PSIG regulated pressure should not necessarily be considered limiting.

The pressure regulator 104 provides therapeutic gas, within a predetermined range of pressures, to an example storage, pressure vessel, or accumulator 106. As the name implies, the accumulator 106 accumulates or holds a predetermined volume of therapeutic gas. The predetermined volume is selected at the design stage based on a host of factors. For example, one consideration in selecting the volume of the accumulator 106 is the response time of the pressure regulator 104 to pressure drops on the downstream side of the pressure regulator 104. For pressure regulators with faster response time, the volume of the accumulator may be lower. Oppositely, for pressure regulators with slower response time, the volume of the accumulator may be higher. Another consideration is that in some cases the system 100 is a portable system carried by the patient. The weight of the example accumulator 106 may increase exponentially with increasing volume. Patients needing oxygen during perambulation are very sensitive to weight of the delivery system, and thus weight considerations drive the design toward smaller accumulators. Another consideration is the range of pressure within the accumulator 106. Putting aside response time of the pressure regulator 104, larger volumes for the accumulator 106 result in smaller pressure drops during bolus delivery, and smaller volumes for the accumulator 106 result in larger pressure drops during bolus delivery. Thus, pressure drop considerations drive the design toward accumulators with larger volume.

Still referring to FIG. 1, the example system further comprises an orifice plate 108 within an orifice. The orifice plate 108 is disposed fluidly between the accumulator 106 and various downstream components (e.g., electrically-controlled valves), discussed more below. The orifice plate 108, and in particular the size (e.g., diameter) of the orifice through the orifice plate 108 is selected at the design stage to set or control a relationship between the bolus delivery time and bolus delivery volume. Other design considerations for the orifice include sound or noise. Smaller orifice sizes result in louder or more noise generation, and larger orifice sizes result in less noise generation. While the example system 100 includes a separate and distinct orifice, the functionality of the orifice plate 108 and orifice may be implemented in any suitable form, such as selecting tubing inside diameter (ID) and length between the accumulator 106 and the various downstream components (e.g., electrically-controlled valves) that provides the functionality of the orifice plate.

In accordance with one example system, for a pressure regulator 104 having a set point downstream pressure of about 25 PSIG, the accumulator 106 may have an internal volume of between and including 15 milliliters (mL) and 20 mL, and in one example case has an internal volume of about 10 mL. Further in the example system the orifice of the orifice plate 108 has a circular aperture with a diameter of between and including 0.5 millimeters (mm) and 1.5 mm, and in one case a diameter of about 1.0 mm. The example pressure set point, volume of the accumulator, and size of the orifice, and taking into account other flow paths to the patient (e.g., lumens of a nasal cannula) results in an approximately linear relationship between bolus delivery time and bolus delivery volume. In particular, the example relationships results in about 10 mL of therapeutic gas delivery for each 100 milliseconds (ms) of delivery time. Such a linear relationship makes programming and control of the system 100 easier to implement. Thus, for a prescription titration volume of 30 mL, the example delivery system may open to flow one or more of the flow control valves for 300 ms. As another example, for a prescription titration volume of 60 mL, the example delivery system may open to flow one or more of the flow control valves for 600 ms.

The system 100 couples to a patient (not shown) by way of a variety of ports or hose connections, such as naris hose connections 110 and 112, and an oral hose connection 114. For example, the system 100 may couple to a patient's nares by way of the nasal cannula, and lumens of the nasal cannula couple to the naris hose connections 110 and 112. In accordance with at least some embodiments, the system 100 monitors patient breathing and delivers therapeutic gas to a left naris (LN), a right naris (RN), or to the mouth (M) of the patient when open to flow. More particularly, in cases where only one breathing orifice is open to flow, the system 100 delivers to only one breathing orifice. In cases where two or more breathing orifices are open to flow, the example system 100 alternates the delivery location, mutually exclusively.

In accordance with at least some embodiments, the system 100 comprises both electrical components and mechanical connections. In order to differentiate between electrical connections and mechanical connections, FIG. 1 (and the remaining figures) illustrate electrical connections between components with dashed lines, and fluid connections (e.g. tubing connections between devices) with solid lines. The example system 100 of FIG. 1 comprises controller 116. The example controller 116 may drive on/off or Boolean signals, such as signals to control the state of the various electrically-controlled valves. Moreover, the example controller 116 may read analog signals (e.g., from various sensors) indicative inhalations through the breathing orifices.

The example system 100 thus comprises electrically-controlled valves in the form of three-port valve 118, three-port valve 120, and three-port valve 122. In accordance with various embodiments, each of these three-port valves may be a five-volt solenoid operated valve that selectively couples one of two ports to a common port (each common port labeled as C in the figure). Three-port valves 118, 120, and 122 may be Humprey Mini-Mizers having part No. D3061, such as may be available from the John Henry Foster Co., or equivalents. Each three-port valve 118, 120, and 122 is electrically coupled to the controller 116. By selectively applying voltage from the controller 116 on a respective electrical connection, the controller 116 may be able to control the state of the system 100. For example, with respect to the three-port valve 118, the three-port valve 118 may: couple gas from the accumulator 106 and/or pressure regulator 104 to the common port and therefore to the example left naris; and couple a sensor in the example form of pressure sensor 124 to the common port and therefore the example left naris. Likewise, the three-port valve 120, under command of the controller 116, may: couple gas from the accumulator 106 and/or pressure regulator 104 to the common port and therefore the example right naris; and couple a sensor in the example form of pressure sensor 126 to the common port and therefore the example right naris. Further still, three-port valve 122 under command from the controller 116 may: couple gas from the accumulator 106 and/or pressure regulator 104 to the common port and therefore the patient's mouth; and couple a sensor in the example form of pressure sensor 128 to the common port and therefore the mouth.

The example pressure sensors 124, 126, and 128 are electrically coupled to the controller 116 such that the controller 116 can read the pressure and/or flow sensed by each. More particularly, the controller 116 may read values indicative of airflow (e.g., inhalation by the patient) through each respective breathing orifice. In alternative embodiments, the pressure sensors 124, 126, and 128 couple to the common ports of the three-port valves 118, 120, and 122, respectively, if the pressure sensors can withstand the pressure of the therapeutic gas during bolus delivery without damage. Regardless of the precise placement, the controller 116 may be able to determine when the patient is inhaling, and in some cases an indication of how much of the air drawn by the patient flows through each of the monitored breathing orifices.

Consider a situation where the system 100 couples to the nares of the patient by way of a bifurcated nasal cannula. As the patient inhales, outlet ports in the nasal cannula proximate to the openings of each naris experience a drop in pressure. The drop in pressure may be sensed through the nasal cannula and associated tubing by each of the pressure sensors 124 and 126. Likewise, a sensing and delivery tube may be placed proximate to the patient's mouth, and thus the pressure sensor 128 may detect an oral inhalation by the patient. In accordance with various embodiments, the system 100 senses whether a patient has airflow through a monitored breathing orifice. If only one breathing orifice is open to flow, the example system 100 delivers therapeutic gas to the breathing orifice open to flow.

Still considering the situation where the patient couples to the system 100 by way of a bifurcated nasal cannula and a separate sensing and delivery tube for the mouth, if there is no obstruction to inhalation in either the nares or the mouth, therapeutic gas may be provided to only one breathing orifice in each inhalation, with the delivery location alternating between the open breathing orifices in subsequent inhalations. Should one naris of the patient become congested or blocked, with respect to the remaining breathing orifices, the delivery location of the therapeutic gas may alternate, mutually exclusively, among the remaining breathing orifices. In some cases, the delivery location is changed for each inhalation. In other cases, the therapeutic gas may be delivered to only one breathing orifice for a plurality of breaths, and then the delivery location may alternate to the next open breathing orifice in the group.

Consider, as an example, that the system 100 of FIG. 1 is coupled to a patient by way of a bifurcated nasal cannula, and that a connection to the patient's mouth is omitted. Further consider that the system 100 senses that both nares are open to flow. In the example situation, the system 100 may deliver therapeutic gas by: delivering therapeutic gas to only the left naris; and then delivering therapeutic gas to only the right naris; and then repeating. In some cases, the transition from delivery to the left naris to delivery to right naris may be after a single inhalation. In other cases, the transition from delivery to the left naris to delivery to the right naris may be after a first number of inhalations. That is, the example the system 100 may deliver only to the left naris for the first number of inhalations, and then the system 100 may deliver only to the right naris for a second number of inhalations. In some cases, the first number of inhalations and the second number inhalations have the same value, but such is not strictly required.

Still referring to FIG. 1. In accordance with example embodiments, delivery of a bolus of therapeutic gas to a breathing orifice may be considered to have a first portion and a second portion owing to the response time of the pressure regulator 104. In particular, during an initial portion of a delivery of a bolus of therapeutic gas, therapeutic gas is delivered only from the accumulator 106. Thereafter, during a second portion of each inhalation, the example system 100 dispenses therapeutic gas from the accumulator 106 and therapeutic gas through the pressure regulator 104. Consider, as an example, delivery to the left naris. During a prior exhalation all of the three-port valves 118, 120, and 122 are closed. The pressure regulator 104 recharges or fills the accumulator 106 with therapeutic gas, and the pressure downstream from the pressure regulator 104 reaches its upper control limit. Thus, during the prior exhalation the pressure regulator 104 fully closes. When the system 100, and particularly the pressure sensor 124 and controller 116, sense an inhalation, the controller 116 commands the three-port valve 118 to change valve positions such that the accumulator 106 is fluidly coupled (through the orifice plate 108) to the left naris hose connection 110 and thus the left naris. Therapeutic gas starts to flow immediately from the accumulator 106, through the orifice of the orifice plate 108, through the electrically-controlled valve, through the left naris hose connection 110, through a lumen of the nasal cannula, and ultimately to the left naris. As the therapeutic gas flows, the pressure downstream of the pressure regulator 104 falls. However, keeping in mind that therapeutic gas (e.g., oxygen) is compressible, and further keeping in mind that the response time of the pressure regulator 104 cannot be instantaneous, initially or during a first portion of the inhalation the therapeutic gas is supplied only from the accumulator 106. When the pressure downstream of the pressure regulator 104 drops sufficiently and/or after the reaction time of the pressure regulator 104 is met, the pressure regulator 104 opens to enable flow through the pressure regulator 104. Thus, during a second portion of the delivery of the bolus the therapeutic gas is from both the pressure regulator 104 and the accumulator 106.

The various embodiments discussed to this point address (at least in part) issues associated with potential shortcomings in the flow of therapeutic gas caused by response time of the pressure regulator 104. As mentioned above, however, in the design of delivery devices, sound and noise considerations favor lower pressure of therapeutic gas delivery, and lower velocity. In order to at least partially counteract a delivery pressure and velocity selection, at least some example embodiments implement flow straighteners within the therapeutic gas flow to reduce turbulence. That is, turbulence of the therapeutic gas flow results in lower average velocity in movement toward the lungs. Turbulence may be introduced in many ways. For example, flowing the therapeutic gas through the orifice of the orifice plate 108 may introduce turbulence. Sharp turns in flow lumens through which the therapeutic gas flows may introduce turbulence, such as within the electrically-controlled valves. Relatedly, each electrically-controlled valve has a valve seat and a moveable member, and when the moveable member is repositioned to enable flow, the flow pathway through the valve seat represents an orifice that introduces turbulence.

In order to reduce turbulence, the example system 100 implements a flow straightener within the flow pathway to each hose connection (and thus to each breathing orifice). For example, the system 100 implements a flow straightener 130 disposed within the fluid pathway between the outlet port (i.e., the common port) of the three-port valve 118 and the left naris hose connection 110. Similarly, the system 100 implements a flow straightener 132 disposed within the fluid pathway between the outlet port of the three-port valve 120 and the right naris hose connection 112. Finally, the system 100 implements a flow straightener 134 disposed within the fluid pathway between the outlet port of the three-port valve 122 and the oral hose connection 114. The flow straighteners 130, 132, and 134 may take any suitable form, such as a plurality of walls or channels within the fluid pathway to make the flow of therapeutic gas closer to laminar flow. Regardless of how the flow straighteners 130, 132, and 134 are implemented, making the therapeutic gas flow more laminar may increase the average velocity in the direction of the patient, may enable the therapeutic gas flow to travel further into the lungs, and may reduce irritation and damage to the mucosal membranes. The specification now turns to example implementations of the system 100.

The system 100 itself may take several forms. In some cases, the system 100 may be an integrated system in which the patient leases, rents, or buys the entire system. For example, when the gas source 102 is a bottle of therapeutic gas, the bottle, pressure regulator 104, accumulator 106, and the remaining valves and sensors may be a single product. In other cases, the gas source 102 may be coupled to an integrated system that comprises the pressure regulator 104, the accumulator 106, and the remaining valves and sensors, as shown by dashed line 136. In yet still further cases, the pressure regulator 104, the accumulator 106, and the orifice plate 108 may be an integrated component, as shown by dashed line 138. The integrated component may then fluidly couple to a delivery system, such as shown by dashed line 140. Thus, the specification contemplates all such variations.

Figure 2A:
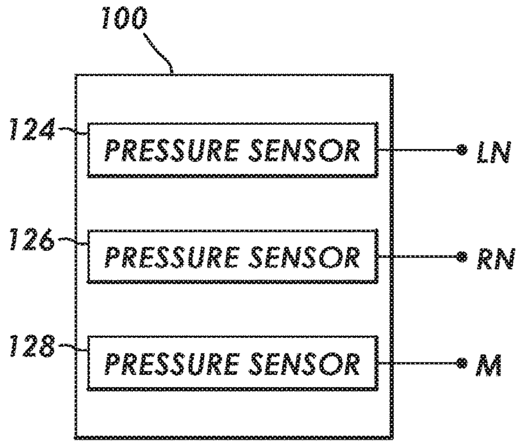
FIG. 2A illustrates the system FIG. 1 in a shorthand notation.
Figure 2B:
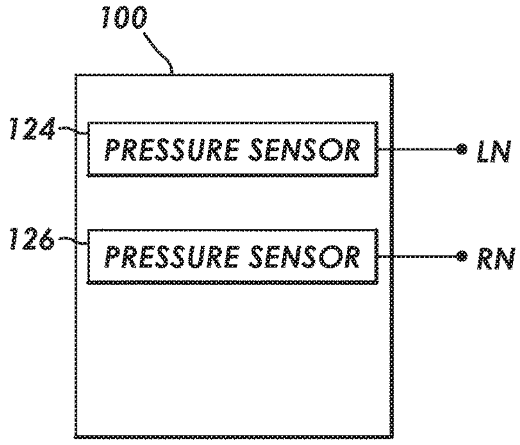
FIG. 2B shows a delivery system in accordance with at least some embodiments.
Figure 2C:
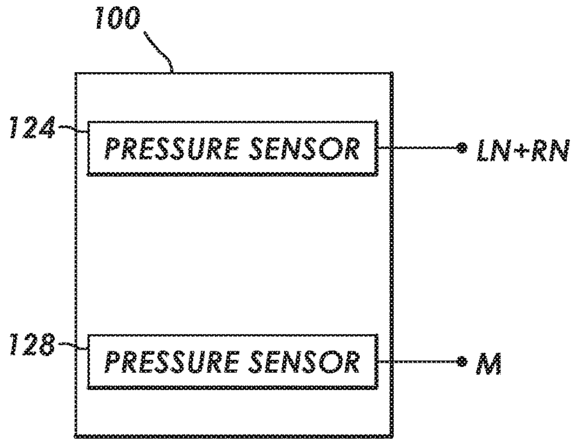
FIG. 2C shows a delivery system in accordance with at least some embodiments.

FIG. 2A illustrates the system 100 of FIG. 1 in a shorthand notation, showing only pressure sensors 124, 126, and 128 coupled to the respective breathing orifices. FIG. 2B illustrates alternative embodiments of the system 100 coupled only to the nares of a patient. In the embodiments of FIG. 2B, if both the left naris and right naris are open to flow, the system 100 alternates delivery location (e.g., left naris, then right naris, then left naris, etc.). In the event that either the left or right naris become clogged or blocked, or if the sensing and delivery tubing (such as a nasal cannula) become dislodged, the system 100 provides the bolus during each inhalation to the naris where airflow is sensed. FIG. 2C illustrates alternative embodiments where two pressure sensors are used, but in this case only one pressure sensor is associated with the nares, and the second pressure sensor is associated with the mouth. In the embodiments of FIG. 2C, a patient may utilize a single lumen cannula associated with the nares and a second sensing and delivery tube associated with the mouth. When both the nares as a group and the mouth are open to flow, the system 100 alternates delivery location (e.g., nares, then mouth, then nares, etc.). In the event that either of the nares as a group or the mouth become blocked or otherwise unavailable for inspiration, the system 100 provides the bolus to the breathing orifice through which inhalation takes place.

Figure 3:
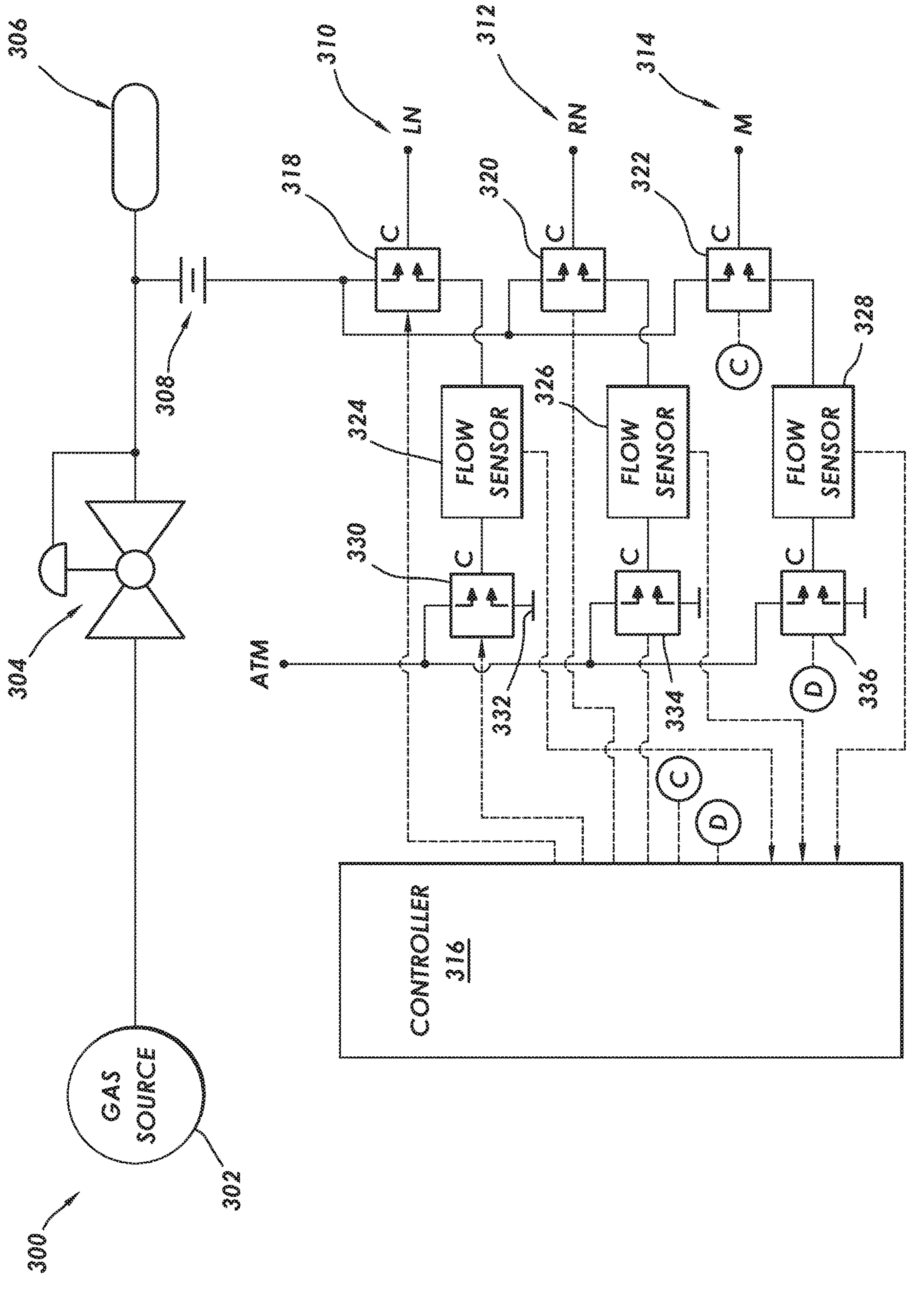
FIG. 3 shows a delivery system in accordance with at least some embodiments.

FIG. 3 illustrates a system 300 constructed in accordance with alternative embodiments. Like the system of FIG. 1, the example system 300 comprises a gas source 302. The gas source 302 couples to a pressure regulator 304 and accumulator 306. The therapeutic gas held by the accumulator 306 is coupled to the delivery system components by way an orifice plate 308 and orifice therein. The set point pressure of the pressure regulator 304, volume of the accumulator 306, and size of the orifice through the orifice plate 308 are selected taking into consideration all the factors noted above with respect to the system of FIG. 1.

The system 300 couples to a patient (not shown) by way of a variety of hose connections, such as naris hose connections 310 and 312, and an oral hose connection 314. As before, the example system 100 monitors patient breathing and delivers therapeutic gas to a left naris, a right naris, or to the mouth of the patient when open to flow. More particularly, in cases where only one breathing orifice is open to flow, the system 300 delivers to only one breathing orifice. In cases where two or more breathing orifices are open to flow, the example system 300 alternates the delivery location, mutually exclusively.

The system 300 comprise a controller 316, and electrical connections to the controller are shown in dashed lines as before. The example system 300 thus comprises electrically-controlled valves in the form of three-port valve 318, three-port valve 320, and three-port valve 322, such as the Humprey Mini-Mizers discussed above. With respect to the three-port valve 318, the three-port valve 318 may: couple gas from the accumulator 306 and/or pressure regulator 304 to the common port and therefore to the example left naris; and couple a sensor in the example form of a flow sensor 324 to the common port and therefore the example left naris. Likewise, the three-port valve 320, under command of the controller 316, may: couple gas from the accumulator 306 and/or pressure regulator 304 to the common port and therefore the example right naris; and couple a sensor in the example form of a flow sensor 326 to the common port and therefore the example right naris. Further still, three-port valve 322 under command from the controller 316 may: couple gas from the accumulator 306 and/or pressure regulator 304 to the common port and therefore the patient's mouth; and couple a sensor in the example form of a flow sensor 328 to the common port and therefore the mouth.

The example flow sensors 324, 326, and 328 are electrically coupled to the controller 316 such that the controller 116 can read indications of flow sensed by each flow sensor. More particularly, the controller 316 may read values indicative of flow through each flow sensor (e.g., inhalation by the patient) and thus through each respective breathing orifice. In alternative embodiments, the flow sensors 324, 326, and 328 may couple to the common ports of the valves 318, 320, and 322, respectively, if the flow sensors can withstand the pressure of the therapeutic gas during bolus delivery without damage. Regardless of the precise placement, the controller 316 may be able to determine when the patient is inhaling, and an indication of how much of the air drawn by the patient flows through each of the monitored breathing orifices.

The pressure sensors of the system 100 of FIG. 1 measure a value indicative pressure, but do not allow gas flow through the pressure sensors. In the example system 300 of FIG. 3, each of the flow sensors is designed and constructed to enable gas flow through the sensor, hence the reason for the terminology "flow sensor." An issue with use flow sensors is the possibility of reverse flow. That is, and considering flow sensor 324 as representative, during a period of time when the system 300 provides therapeutic gas to the left naris, the three-port valve 318 provides the therapeutic gas to the left naris and blocks flow through the flow sensor 324. After the bolus delivery ends, the three-port valve 318 changes valve position and thus fluidly couples the flow sensor 324 to the common port and therefore the example left naris. If the flow sensor 324 outlet is not blocked, a portion of the therapeutic gas may reverse flow through the flow sensor 324. Thus, in the example system an electrically-controlled valve in the form of three-port valve 330 couples between the flow sensor 324 and the atmospheric vent (labeled ATM in the figure).

Three-port valve 330, in a first valve position, couples the flow sensor 324 to the atmospheric vent ATM, thus enabling gas flow through the flow sensor 324 for measurement purposes. The three-port valve 330, in a second valve position, couples the flow sensor 324 to a blocked port 332. Consider, as an example, that after a bolus has been delivered, the three-port valve 318 may change valve positions, thus fluidly coupling the flow sensor 324 to the common port and the example left naris. If the flow sensor 324 outlet is not blocked, a portion of the therapeutic gas may reverse flow through the flow sensor 324 and out the atmospheric vent. Three-port valve 330 (as well as corresponding three-port valves 334 and 336) may be used to temporarily block reverse flow and loss of therapeutic gas. In some cases, the valves 330, 334, and 336 may remain in a position that blocks flow for about 300 milliseconds after therapeutic gas delivery has stopped by a change of valve position by upstream three-port valves 318, 320, and 322. After the expiration of the period of time of possible reverse flow has ended, one or more of the three-port valves 330, 334, and 336 may change valve positions, thus enabling the flow sensors to sense airflow (e.g., an inhalation). The description with respect to the three-port valves 318 and 330, and flow sensor 324 for the left naris is equally applicable for the corresponding structures for the right naris and the mouth.

Figure 4A:
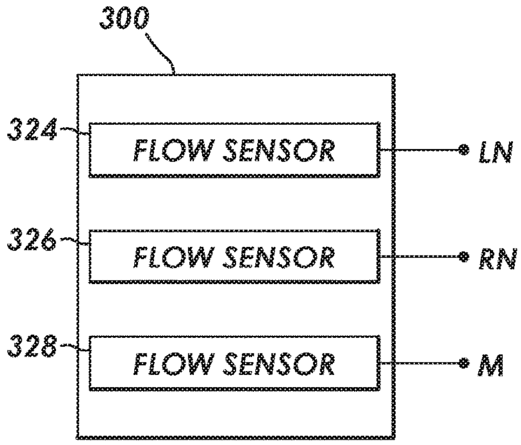
FIG. 4A illustrates the delivery system of FIG. 3 in a shorthand notation.
Figure 4B:
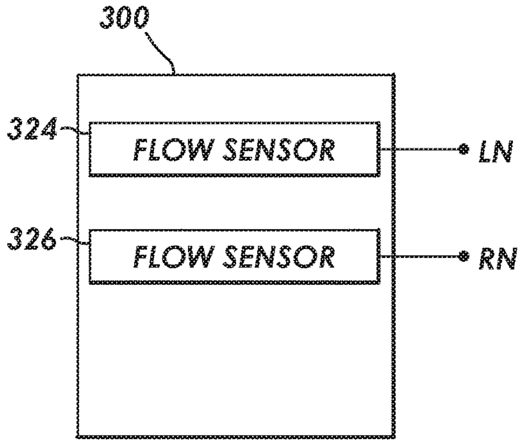
FIG. 4B shows a delivery system in accordance with at least some embodiments.
Figure 4C:
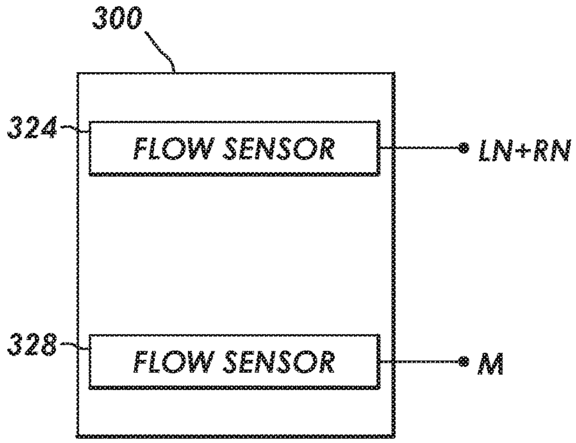
FIG. 4C shows a delivery system in accordance with at least some embodiments.

FIG. 4A illustrates the system 300 of FIG. 3 in a shorthand notation, showing only flow sensors 324, 326, and 328 coupled to their respective breathing orifice. FIG. 4B illustrates alternative embodiments where only a patient's nares are used for sensing and delivery. In the embodiments of FIG. 4B, if both the left naris and right naris are open to flow, the system 300 delivers therapeutic gas in an alternating fashion. In the event that either the left naris or the right naris become clogged or blocked, or if the sensing and delivery tubing (such as a nasal cannula) become dislodged, the delivery system provides the bolus only to the naris where airflow is sensed. FIG. 4C illustrates further alternative embodiments where two flow sensors are used, but in this case only one flow sensor is associated with the nares, and the second flow sensor associated with the mouth. In the embodiments of FIG. 4C, a patient may utilize a single lumen cannula associated with the nares, and a second sensing and delivery tube associated with the mouth. If both the nares as a group and the mouth are open to flow, the system 100 delivers therapeutic gas in an alternating fashion (e.g., nares, then mouth, then nares, etc.). In the event that either of the nares as a group or the mouth become blocked or otherwise unavailable for inspiration, the system 100 provides the bolus to the breathing orifice through which inhalation takes place.

Returning to FIG. 3. In FIG. 3 each flow sensor 324, 326, and 328 is associated with a three-port valve 330, 334, and 336, respectively. In yet still further embodiments, the common connection of a single three-port valve may fluidly couple to all three flow sensors, and thus a single valve may simultaneously block reverse flow through the flow sensors. Further, while FIG. 3 shows exclusive use of flow sensors, and FIG. 1 shows exclusive use of pressure sensors, the various embodiments need not be so limited. For example, the nares may be associated with pressure sensors, and the mouth may be associated with a flow sensor. Oppositely, the nares may be associated with flow sensors, and the mouth may be associated with a pressure sensor. One of ordinary skill in the art, with the benefit of this disclosure and now understanding the function of each type of sensor, could design and construct a mixed-sensor system.

Figure 5:
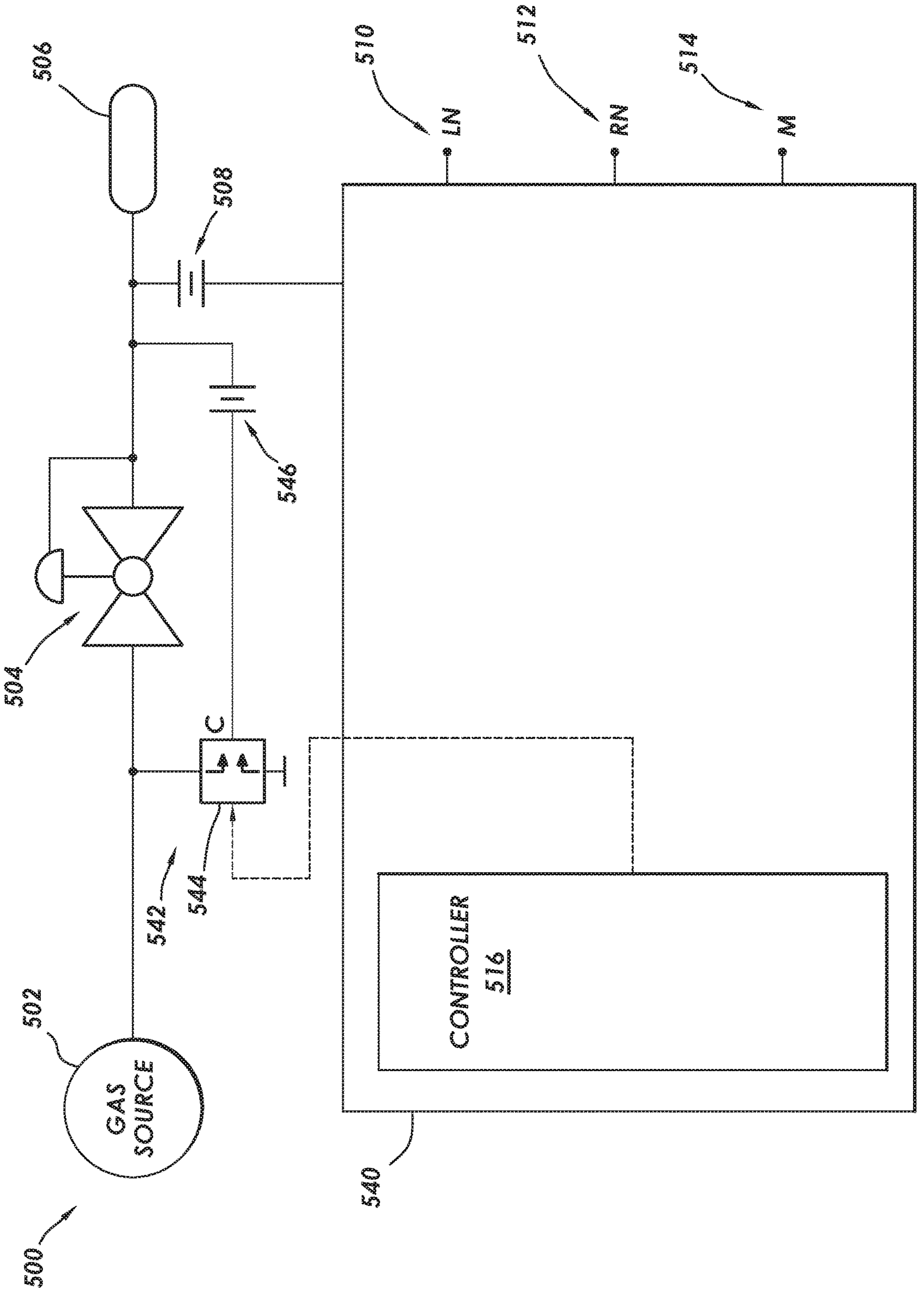
FIG. 5 shows a delivery system in accordance with at least some embodiments.

FIG. 5 shows a system 500 in accordance with at least some embodiments. The example system 500 comprises a gas source 502 and a pressure regulator 504. As with the prior embodiments, the example pressure regulator 504 provides therapeutic gas, within a predetermined range of pressures, to an example accumulator 506. The example system 500 further comprises an orifice plate 508 with an orifice defined therein. The orifice plate 108 is disposed fluidly between the accumulator 506 and various downstream components of a delivery system 540. The example delivery system 540 comprises a controller 516. The example delivery system 540 further includes various electrically-controlled valves and sensors such that therapeutic gas can be selectively delivered to any of the left naris hose connection 510 (and thus the left naris), the right naris hose connection 512 (and thus the right naris), and the oral hose connection 514 (and thus the mouth). The internal components that sense inhalations and delivery therapeutic gas are omitted from FIG. 5 so as not do unduly complicate the figure. The internal components may be same as FIG. 1, the same as FIG. 5, combinations of FIGS. 1 and 5 (see, e.g., FIGS. 2A-2C and 4A-4C), or equivalents.

The example system 500 FIG. 5 includes additional components to reduce the effect of the response time of the pressure regulator 504 and/or to reduce the size and weight of the accumulator 506. In particular, the example system 500 of FIG. 5 further comprises bypass tubing 542 around the pressure regulator 504. An electrically-controlled valve in the example form a three-port valve 544 and an orifice in the example form of an orifice plate 546 with an orifice plate are fluidly coupled within the bypass tubing 542. The three-port valve 544 has a first port that fluidly couples to the upstream side of the pressure regulator 504. The three-port valve 544 has a second port that is blocked, and a common port. In the example layout, the common port fluidly couples to one side of the orifice plate 546, and the second side of the orifice plate 546 fluidly couples downstream of the of the pressure regulator 504 (e.g., fluidly couples to the accumulator 506). The example three-port valve 544 is electrically coupled to the controller 516 as shown by the dashed line. Thus, under command of the controller 516, the three-port valve 544 may: couple a bypass flow of therapeutic gas through the bypass tubing 542 to the accumulator 506 and/or the orifice plate 508; and couple the blocked port to the common port which blocks the bypass flow through bypass tubing 542, and blocks any reverse flow through the orifice plate 546. In the example of FIG. 5, the orifice plate is downstream from the three-port valve 544 in the bypass flow direction. However, the orifice plate 546 may alternatively be placed upstream of the three-port valve 544. Further still, the functionality of the orifice of the orifice plate 546 (e.g., to limit bypass flow), may be implemented in any suitable form, such as selecting tubing with an internal diameter small enough to limit the bypass flow the designed bypass flow rate.

As before, the example pressure regulator 504 is selected, designed, or constructed to have a set point downstream of about 25 PSIG. Also as before, the pressure regulator 504 has a non-zero response time with respect to drop in the downstream pressure. The embodiments of FIG. 5 address, at least in part, response time issues by selectively providing a bypass flow of therapeutic gas around the pressure regulator 504. The example bypass flow may implement several functions. Firstly, the bypass flow may help hold or maintain the pressure in the accumulator 506 within a smaller range of pressures during delivery of therapeutic gas. Another function may be to enable use of an accumulator 506 of smaller volume (compared, for example, to the FIGS. 1 and 5).

In accordance with example embodiments, delivery of a bolus of therapeutic gas to a breathing orifice may again be considered to have a first portion and a second portion. In particular, during a first portion of a delivery of a bolus of therapeutic gas, therapeutic gas is delivered from the accumulator 106 and through bypass tubing 542. Stated another way, when the controller 516 activates a valve in the delivery system 540 to begin to provide a bolus of therapeutic gas to the patient, the controller 316 substantially simultaneously changes the valve position of three-port valve 544 to enable the bypass flow. Thereafter, during a second portion of each inhalation, the example system 100 dispenses therapeutic gas from the accumulator 106 and through the pressure regulator 104. During the second portion, the bypass flow through the bypass tubing 542 may continue, or once the pressure regulator 504 opens to flow the three-port valve 544 may change valve position to halt or cease the bypass flow.

Consider, as an example, delivery to the left naris. During a prior exhalation, the pressure regulator 504 recharges or fills the accumulator 506 with therapeutic gas, and the pressure downstream from the pressure regulator 504 reaches its upper control limit. Thus, during the prior exhalation the pressure regulator 504 fully closes and the bypass flow through the bypass tubing 542 is blocked. When the system 500 senses an inhalation, the controller 516 commands delivery of therapeutic gas to the example left naris hose connection 510 (and thus the left naris). Therapeutic gas starts to flow immediately from the accumulator 506, through the orifice of the orifice plate 508, through the left naris hose connection 110, through a lumen of the nasal cannula, and ultimately to the left naris. Contemporaneously with commanding delivery of therapeutic gas to the left naris (e.g., simultaneously), the controller 516 may initiate the bypass flow through the bypass tubing 542 by commanding the three-port valve 544 to change valve positions. Thus, during the first portion of the inhalation the therapeutic gas is supplied from the accumulator 506 and through the bypass tubing 542. When the pressure downstream of the pressure regulator 504 drops sufficiently and/or after the reaction time of the pressure regulator 504 is met, the pressure regulator 504 opens to enable flow through the pressure regulator 504.

Thus, during a second portion of the delivery of the bolus of therapeutic gas is from both the pressure regulator 504 and the accumulator 506.

During an inhalation, the controller 516 may cease flow through the bypass tubing 542 at any suitable time by commanding the three-port valve 544 to change valve positions and thus blocking the bypass flow through the bypass tubing. Determining the length of time bypass flow through the bypass tubing 542 is enabled may take many forms. In one example case, the bypass flow through the bypass tubing 542 may take place for a predetermined amount of time based on the response time of pressure regulator 504 (and based on the size of the orifice limiting the bypass flow). In yet still other cases, the controller 516 may enable the therapeutic gas to flow through the bypass tubing 542 for an amount of time that is variable and based on the prescription titration volume and/or the amount of time therapeutic gas is delivered to the patient. For example, the controller 516 may enable bypass flow through the bypass tubing 542 for an amount of time being a predetermined percentage (e.g., 5%, 10%) of the bolus delivery time to the patient. If the controller 516 plans to deliver, for example, a bolus of 60 mL (e.g., by flowing therapeutic gas for 600 ms), the controller 516 may enable bypass flow through the bypass tubing 542 for 60 ms to help maintain the pressure until pressure regulator 504 opens to flow.

In yet still further cases, the controller 516 may only enable the bypass flow through the bypass tubing 542 when the size of the bolus is above a predetermined volume and/or the amount of time therapeutic gas is to be delivered is above a predetermined time. For example, the controller 516 may refrain from enabling bypass flow through the bypass tubing 542 for smaller bolus sizes (e.g., refrain for bolus sizes of 32 mL or less). The refraining from enabling the bypass flow through the bypass tubing 542 for smaller bolus sizes may be based on an assumption, or based on empirical testing, that the accumulator 506 and pressure regulator 504 can adequately supply the volume. However, the controller 516 may enable bypass flow through the bypass tubing 542 for larger bolus sizes (e.g., enable the bypass flow bolus sizes of greater than 32 mL) based on an assumption, or based on empirical testing, that pressure downstream of the pressure regulator 504 may fall below a predetermined pressure (thus adversely affecting bolus size and velocity) in the absence of the bypass flow.

In yet still further cases, the bypass tubing 542 and related three-port valve 544 and orifice may be implemented to reduce the size of the accumulator 506 without regard to response time of pressure regulator 504. That is, by enabling the bypass flow through the bypass tubing 542, the volume of the accumulator 506 may be smaller than cases that do not implement the bypass tubing 542

The specification now turns to a more detailed discussion of operating any of the example systems 100, 300, and/or 500. Referring to system 100 as representative, when only one breathing orifice is open to flow the example systems provide the bolus of therapeutic gas to the only breathing orifice open to flow. If more than one breathing orifice is open to flow, then the example systems alternate in some fashion between the breathing orifices open to flow. In an ideal situation the example systems would simultaneously detect that breathing orifices are open to flow, and make a decision about delivery location. However, for a variety of reason simultaneous detection may not be possible. For example, the controller 116 may be programmed to cycle through reading values from the various pressure and/or flow sensors, and thus the first breathing orifice found to be open to flow may have been first only from a sampling standpoint. Moreover, anatomical differences between breathing orifices of the patient may cause inhalation to be sensed at a first breathing orifice before a second breathing orifice though both are technically open to flow. Thus, a certain amount of hysteresis may be used in the detection and delivery system.

Consider a situation where the representative system 100 is providing therapeutic gas only to the nares of a patient (i.e., there is no oral sensing or delivery). Further consider that both the patient's nares are blocked. The example system, not sensing either breathing orifice is open to flow, may refrain from providing therapeutic gas to the patient. In actual circumstance an alarm may sound under this assumption, and/or the example system may go to continuous mode in the hope of providing at least some oxygen to the patient. If at any point the example system senses inhalation through the left nariss, then a bolus of therapeutic gas is provided to the left naris during the inhalation. Further consider that having a single naris, here the left naris, open to flow continues for several inhalations and each time the example system provides a bolus to the left naris.

Now consider that in a subsequent inhalation the representative system 100 again senses flow in the left naris and begins bolus delivery, but during the inhalation also senses flow in the right naris (i.e., there is a time delay in sensing the flow in the right naris). The example system stores the information about the right naris, such as setting a dual flag indicating both nares open to flow, and setting a location flag indicating the last delivery was to the left naris. In a subsequent inhalation (e.g., an immediately subsequent inhalation), the example system may first sense flow in the left naris but may refrain from providing a bolus to the left naris (because of one or both of the flags), and then provide the bolus to the right naris as soon as flow is detected in the right naris. The example system would leave the dual flag asserted (as again both nares are open to flow), and toggle the location flag indicating the last delivery was to the right naris. In a next subsequent inhalation (e.g., an immediately subsequent inhalation), the example system may first sense flow in the left naris and deliver to the left naris, but again also eventually sense flow in the right naris. The example system would again leave the dual flag asserted, and toggle the location flag indicating the last delivery was to the left naris. The process continues as long as both nares are open to flow.

Now consider that the left naris becomes clogged or blocked to flow during a delivery to the right naris. That is, during a particular inhalation the bolus is delivered to the right naris, but the example system fails to detect flow in the left naris. In this situation the example system would de-assert the dual flag (as now only one naris is open to flow), and toggle the location flag indicating the last delivery was to the right naris. In a subsequent inhalation where the left naris remains blocked to flow, as soon as the inhalation is detected for the right naris, the bolus of therapeutic gas is delivered to the right naris.

With the benefit of this disclosure, one of ordinary skill in the art extend to a three breathing orifice case that takes into account delays in sensing inhalations. Moreover, overrides would be present in each situation such that if the example system intends to deliver to a particular breathing orifice, but flow fails to materialize in a certain amount of time, then the system defaults back to delivery to a breathing orifice open to flow where flow has been sensed.

Figure 6:
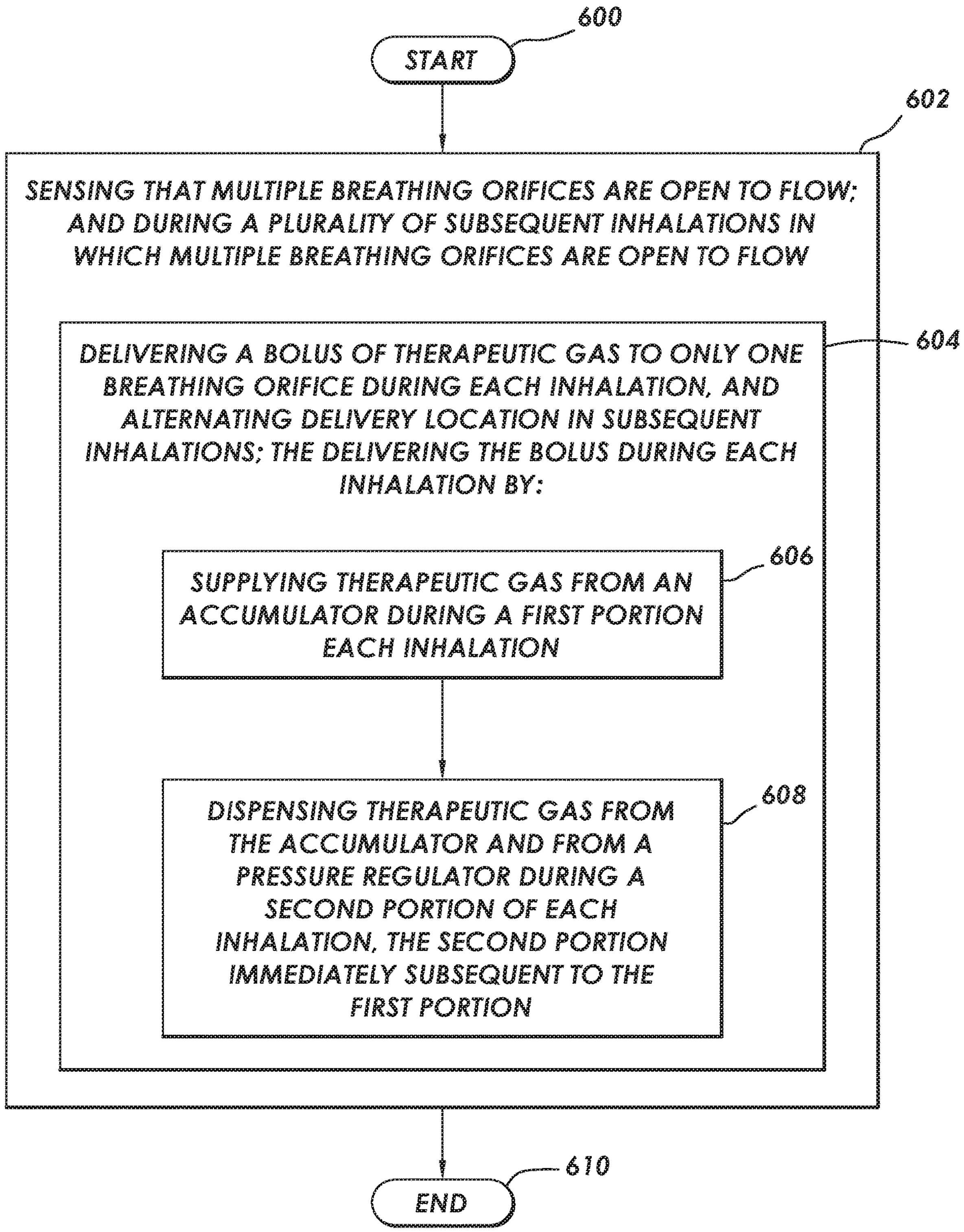
FIG. 6 shows a method in accordance with at least some embodiments.

FIG. 6 shows a method in accordance with at least some embodiments. In particular, the method starts (block 600)

and comprises sensing (e.g., by a delivery device), that multiple breathing orifices are open to flow (block 602). During each sensing where multiple breathing orifices are open to flow, the method may comprise delivering a bolus of therapeutic gas to only one breathing orifice during each inhalation, and alternating delivery location in subsequent inhalations (block 604). The delivering in each inhalation may comprise: supplying therapeutic gas from an accumulator during a first portion each inhalation (block 606); and dispensing therapeutic gas from the accumulator and from a pressure regulator during a second portion of each inhalation, the second portion immediately subsequent to the first portion (block 608). In some cases the, supplying therapeutic gas during the first portion (again block 608) is supplying only from the accumulator. In other cases, however, the supplying therapeutic gas during the first portion (again block 608) is supplying from the accumulator and through bypass tubing that bypasses the pressure regulator. Thereafter the method ends (block 610).

Figure 7:
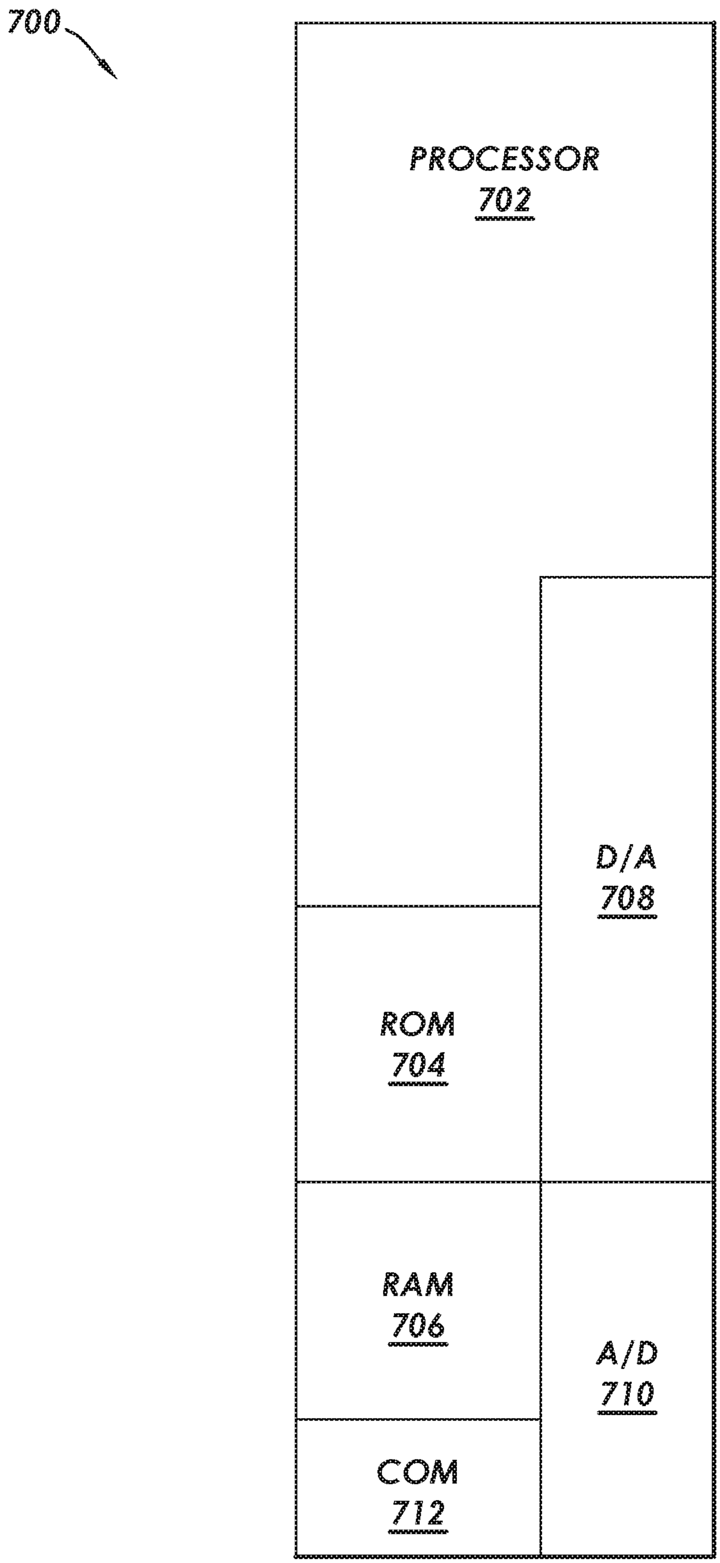
FIG. 7 shows a controller in accordance with at least some embodiments.

FIG. 7 shows a controller 700 in accordance with at least some embodiments. In particular, controller 700 may be an example of any of the previously discussed controllers, such as controller 116, controller 316, and/or controller 516. The example controller 700 may be microcontroller, and therefore the microcontroller may be integral a processor 702, read only memory (ROM) 704, random access memory (RAM) 706, a digital-to-analog converter (D/A) 708, and an analog-to-digital converter (ND) 710. The controller 700 may further comprise communication logic 712, which enables systems to communicate with external devices, e.g., to transfer stored data about a patient's breathing patterns. Although a microcontroller may be preferred because of the integrated components, in alternative embodiments the controller 700 may be implemented by a stand-alone processor 702 in combination with individual RAM, ROM, communication, D/A and ND devices.

The ROM 704 stores instructions executable by the processor 702. In particular, the ROM 704 may comprise a software program or instructions that, in whole or in part, implements the various embodiments discussed herein. The RAM 706 may be the working memory for the processor 702, where data may be temporarily stored and from which instructions may be executed. Processor 702 may couple to other devices within the delivery system by way of A/D converter 710 (e.g., sensors to sense attributes of airflow) and D/A converter 708 (e.g., electrically controlled valves). Thus, the ROM 704, and/or the RAM 706 may be non-transitory computer-readable mediums upon which instructions are stored.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method of providing therapeutic gas to a patient, the method comprising:

sensing, by a delivery device, that multiple breathing orifices are open to flow; and sensing during a plurality of subsequent inhalations in which multiple breathing orifices are open to flow delivering, by the delivery device, a bolus of therapeutic gas to only one breathing orifice during each inhalation, and alternating delivery location in subsequent inhalations;

wherein delivering the bolus of therapeutic gas during each inhalation further comprises:

supplying therapeutic gas only from an accumulator to the only one breathing orifice during a first portion of each inhalation; and then dispensing therapeutic gas from the accumulator and from a pressure regulator to the only one breathing orifice during a second portion of each inhalation, the second portion immediately subsequent to the first portion.

2. The method of claim 1 wherein delivering the bolus further comprises applying the bolus of therapeutic gas to a flow straightener prior to application to the only one breathing orifice in each inhalation, the flow straightener within the flow of therapeutic gas after a control valve and before the therapeutic gas flows into a tube of a cannula.

3. The method of claim 1 wherein supplying therapeutic gas further comprises supplying from the accumulator having a volume greater than 10 milliliters (ml).

4. The method of claim 3 wherein supplying from the accumulator further comprises supplying from the accumulator having a volume greater than 10 ml and through an orifice having a diameter smaller than one millimeter.

5. The method of claim 3 wherein supplying from the accumulator further comprises supplying from the accumulator having a volume of between and including 15 ml and 20 ml, and through an orifice having a diameter of between and including 0.5 millimeter (mm) and 1.0 mm.

6. The method of claim 1 wherein sensing that multiple breathing orifices are open to flow and delivering therapeutic gas to only one breathing orifice in each inhalation further comprises:

a) delivering therapeutic gas to only a left nare; and then b) delivering therapeutic gas to only a right nare; and then c) repeating steps a) and b).

7. The method of claim 1 wherein sensing that multiple breathing orifices are open to flow and delivering therapeutic gas to only one breathing orifice in each inhalation further comprises:

a) delivering therapeutic gas over a first number of inhalations only to a left nare; and then b) delivering therapeutic gas over a second number of inhalations only to a right nare; and then c) repeating steps a) and b).

8. The method of claim 7 wherein the first number is equal to the second number.

9. A therapeutic gas delivery device comprising:

a source of therapeutic gas;

a first hose connection configured to fluidly couple to a first lumen of a nasal cannula;

a first sensor associated with the first hose connection;

a second hose connection configured to couple to a second lumen of the nasal cannula;

a second sensor associated with the second hose connection;

an accumulator defining a volume, the accumulator fluidly coupled to the source of therapeutic gas;

a first electrically-controlled valve defining an inlet port and an outlet port, the outlet port fluidly coupled the first hose connection;

a second electrically-controlled valve defining an inlet port and an outlet port, the outlet port of the second electrically-controlled valve fluidly coupled the second hose connection;

an orifice, the inlet port of the first electrically-controlled valve fluidly coupled the accumulator through the orifice, and the inlet port of the second electrically-controlled valve fluidly coupled to the accumulator through the orifice;

a controller electrically coupled to the first and second electrically-controlled valves, and the controller electrically coupled to the first and second sensors, the controller configured to:

sense a first inhalation through the first and second hose connections;

command only the first electrically-controlled valve to fluidly couple the first hose connection to the accumulator during the first inhalation;

sense a second inhalation through the first and second hose connections;

command only the second electrically-controlled valve to fluidly couple the second hose connection to the accumulator during the second inhalation;

deliver therapeutic gas from the accumulator during a first portion of each of the first inhalation and the second inhalation; and deliver therapeutic gas from the accumulator and the pressure regulator during a second portion of each of the first inhalation and the second inhalation.

10. The therapeutic gas delivery device of claim 9 further comprising:

a first flow straightener disposed in a fluid pathway between the first electrically-controlled valve and the first hose connection; and a second flow straightener disposed in a fluid pathway between the second electrically-controlled valve and the second hose connection.

11. The therapeutic gas delivery device of claim 9 further comprising the accumulator defines a volume greater than 10 milliliters (ml).

12. The therapeutic gas delivery device of claim 11 further comprising the orifice defines a diameter smaller than one millimeter, and where the orifice diameter is non-zero.

13. The therapeutic gas delivery device of claim 11 further comprising the accumulator defines a volume of between and including 15 ml and 20 ml, and the orifice defines a diameter of between and including 0.5 millimeter (mm) and 1.0 mm.

14. The therapeutic gas delivery device of claim 9 wherein the second inhalation is immediately subsequent to the first inhalation.

15. A system for delivering therapeutic gas to a patient, comprising:

a source of therapeutic gas;

a pressure regulator, the pressure regulator coupled to the source of therapeutic gas, and the pressure regulator configured to control pressure of therapeutic gas;

an accumulator fluidly coupled to the pressure regulator;

a delivery system comprising:

a first hose connection configured to fluidly couple to a first lumen of a nasal cannula;

a first sensor associated with the first hose connection;

a second hose connection configured to couple to a second lumen of the nasal cannula;

a second sensor associated with the second hose connection;

a first electrically-controlled valve defining an inlet port and an outlet port, the outlet port fluidly coupled the first hose connection;

a second electrically-controlled valve defining an inlet port and an outlet port, the outlet port of the second electrically-controlled valve fluidly coupled the second hose connection;

a controller electrically coupled to the first and second electrically-controlled valves, and the controller electrically coupled to the first and second sensors, the controller configured to:

sense an inhalation through both the first and second hose connections; and alternate delivery, mutually exclusively, of a bolus of therapeutic gas to the first and second hose connections;

wherein the bolus of therapeutic gas alternately delivered to the first and second hose connections includes a first portion of therapeutic gas delivered from the accumulator and a second portion delivered from the accumulator and from the pressure regulator.

16. The system of claim 15:

wherein the delivery system is fluidly coupled to the accumulator; and;

wherein the accumulator is external to the delivery system.

17. The system of claim 15 wherein the delivery system is fluidly coupled the pressure regulator, and the accumulator is internal to the delivery system.

18. The system of claim 15 wherein the delivery system further comprises an orifice plate defining an orifice, the inlet port of the first electrically-controlled valve fluidly coupled the accumulator through the orifice of the orifice plate, and the inlet port of the second electrically-controlled valve fluidly coupled the accumulator through the orifice of the orifice plate.

19. The system of claim 18 further comprising the accumulator defines a volume greater than 10 ml and the orifice defines a diameter smaller than one millimeter.

20. The system of claim 18 further comprising the accumulator defines a volume of between and including 15 ml and 20 ml, and the orifice defines a diameter of between and including 0.5 millimeter (mm) and 1.0 mm.

21. The system of claim 15 further comprising:

a first flow straightener disposed in a fluid pathway between the outlet port of the first electrically-controlled valve the first hose connection; and a second flow straightener disposed in a fluid pathway between the outlet port of the second electrically-controlled valve the second hose connection.

22. The system of claim 15 further comprising the accumulator defines a volume greater than 10 milliliters (ml).

23. The system of claim 15 wherein the source of therapeutic gas is a bottle of therapeutic gas.

* * * * *